United States Patent [19]

Sabb et al.

[11] Patent Number: 4,985,560

[45] Date of Patent: Jan. 15, 1991

[54] PYRIDAZINO(4,5-B)INDOLIZINES

[75] Inventors: Annmarie L. Sabb, Pennington, N.J.; Magid A. Abou-Gharbia, Glen Mills, Pa.; Gervais Dionne, St. Laurent, Canada

[73] Assignee: American Home Products Corporation, New York, N.Y.

[21] Appl. No.: 464,468

[22] Filed: Jan. 12, 1990

[51] Int. Cl.$^5$ .............. C07D 471/14; A61K 31/495; A61K 31/535
[52] U.S. Cl. .................................... 544/115; 544/234
[58] Field of Search ......................... 544/234, 115

[56] References Cited

U.S. PATENT DOCUMENTS 4,735,953  4/1988  Lavretskaya et al. ............ 514/313
4,797,419  1/1989  Moos et al. ...................... 514/588

FOREIGN PATENT DOCUMENTS 205247  12/1986  European Pat. Off. .
0251937  3/1987  European Pat. Off. .

OTHER PUBLICATIONS

Gray et al., *Tips*, pp. 85–88 (Dec. 1989).
Stern et al., *Neurology* 38, pp. 1837–1841 (1988).

*Primary Examiner*—Mukund J. Shah
*Assistant Examiner*—E. Bernhardt
*Attorney, Agent, or Firm*—Richard K. Jackson

[57] ABSTRACT

The compound of the formula:

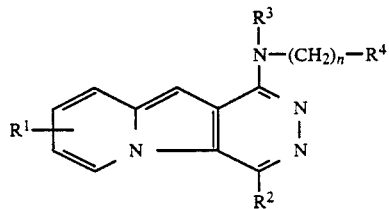

in which $R^1$ is hydrogen, alkoxy, cyano, halo, nitro, amino, or mono- or dialkylamino; $R^2$ is hydrogen, alkyl, phenyl, benzyl, 2-thienyl, 3-thienyl or 2-,3- or 4-pyridinyl; $R^3$ is hydrogen, alkyl or phenyl; $R^4$ is N-methylpyrrolidin-2yl, 2-, 3- or 4-pyridinyl, 3-quinuclidinyl or

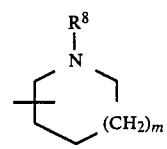

where n is 1 to 5; m is 0 to 3; and $R^8$ is hydrogen or alkyl of 1 to 6 carbon atoms; or $R^4$ is

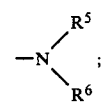

wherein: (a) n is 2, $R^5$ taken with $R^3$ is ethylene and $R^6$ is —CHO, alkyl, unsubstituted or substituted phenyl, pyrimidinyl, pyridinyl, or pyrazinyl, where the substituents are alkyl, alkoxyl, halo, cyano, nitro or trifluoromethyl; (b) n is 1 to 5, and $R^5$ and $R^6$ taken together are polymethylene which may be alkyl substituted or $R^5$ nd $R^6$ are morpholino, 3-azabicyclo[3.2.2]nonan-3-yl, pyrrol-1-yl, pyrrolidin-2-on-1-ytl, pyrrolidin-2-thion-1-yl, imidazol-1-yl, alkyl-piperidin-1-yl or a piperazin-1-yl moiety in the 4-position of which is hydrogen, —CHO, alkyl or unsubstituted or substituted phenyl, pyrimidinyl, pyridinyl, or pyrazinyl, alkoxy, halo, cyano, nitro or trifluoromethyl; or (c) n is 1 to 5, and $R^5$ and $R^6$ are, independently, hydrogen, alkyl, phenyl, 3-quinuclidinyl, 2-adamantyl, bicyclo[3.2.1]octan-1-yl, bicyclo[3.3.1]nonan-9-yl or 2-,3- or 4- pyridinyl; or a pharmaceutically acceptable salt thereof are $M_1$ receptor agonists useful in treatment of dementias involving the cholinergic system.

17 Claims, No Drawings

PYRIDAZINO(4,5-B)INDOLIZINESdd

BACKGROUND OF THE INVENTION

Although some forms of dementia can be treated (ie, dementias resulting from cardiovascular disease, chemical toxins, depression, or head trauma) no effective therapy currently exists for the major form of dementia, senile dementia of the Alzheimer's type (SDAT), which accounts for more than half of all dementias, Moos et al., Med. Res. Reviews 8(3), 353 (1988). The reason for this is that the etiology of the disease has not yet been confirmed, though many theories exist, Henderson, Acta Psychiat. Scand. 78, 257 (1988), Marx, Science 243, 1664 (1989). One theory which has gained wide acceptance is that the cognitive decline observed in patients with Alzheimer's disease and other forms of dementia is related to hypofunction of the cholinergic system, Bartus et al., Science 217 408 (1982), Collerton, Neuroscience 19(1) 1 (1986) and Whitehouse et al., Ann. Neurol., 10 122 (1981). A study comparing patients with Alzheimer's disease (50), other dementias (10), and age-matched controls (20) found that 50–76% of the Alzheimer's patients had a statistically significant loss of cholinergic neurons in the basal forebrain. Other studies have revealed that loss of presynaptic cholinergic neurons in the amygdala, hippocampus and neocortex related to hypofunction of the basal forebrain cholinergic system is also found in Parkinson's disease, Down's syndrome, dementia pugelistica, and some other forms of dementia, Whitehouse et al., Adv. Behav. Biology, 29 85 (1985).

The neurotransmitter of the cholinergic system is acetylcholine. Receptor binding studies on brain tissue from animals (e.g. rats) and humans have identified two major types of acetylcholine (muscarinic) receptors, presynaptic receptors on nerve terminals ($M_2$) and postsynaptic receptors ($M_1$). Postmortem examination of brain tissue from Alzheimer's patients has shown that while postsynaptic $M_1$ receptors remain intact, there is a reduction in the number of presynaptic $M_2$ receptors, Marx, ibid. In fact, there is good correlation between the degree of presynaptic neuronal loss and the severity of the dementia, Marx, ibid, Collerton, ibid.

Degeneration of presynaptic cholinergic neurons results in insufficient production of acetylcholine and understimulated postsynaptic $M_1$ receptors. Memory loss in normal humans, Bartus et al., ibid and Drachman et al., Arch. Neurol. 30 113 (1974) and animals (e.g. cat, rat, and monkey), Bartus et al., ibid and Collerton, ibid can be artificially induced with a muscarinic antagonist, such as scopolamine. This deficit can be reversed by the anticholinesterase inhibitor, physostigmine, in both humans and monkeys, Marx ibid and by the muscarinic agonist arecoline in rats. However, neither physostigmine nor arecoline have clinical efficacy due to undesirable side-effects, a short duration of action and a narrow active dose range. Other therapies examined in clinical studies include treatment of Alzheimer's patients and healthy elderly patients with the acetylcholine precursors choline and lecithin. No significant improvement was observed on any cognitive test.

Over the next 50 years it is predicted that nearly 20% (55 million) of the population in the United States will be over 65 years of age, Moos et al., ibid. Couple this with the fact that Alzheimer's disease alone afflicts between 5 and 15% of individuals over 65 years of age, Collerton, ibid and it becomes obvious that dementia is a major health problem for which there is an urgent need for effective therapy. Centrally acting muscarinic receptor agonists which have greater affinity for the $M_1$ receptor than the $M_2$ receptor as evidenced by in vitro receptor binding studies are useful for the treatment of Alzheimer's disease and other disorders associated with cortical cholinergic hypofunction. $M_1$ receptor agonists have fewer undesirable side effects than muscarinic agonists which are not $M_1$ selective since unwanted peripheral effects are usually associated with agonism of the $M_2$ receptor.

DESCRIPTION OF THE INVENTION

In accordance with this invention, there is provided a group of novel pyridazino[4,5-b]indolizine compounds which are selective agonists for central cholinergic $M_1$ receptors and useful for treatment of diseases involving hypofunction of the cholinergic system. In addition, some of these compounds inhibit platelet aggregation induced by collagen and are useful as antithrombotic agents.

The compounds of the present invention are characterized by the general formula:

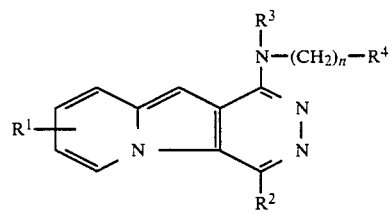

in which
$R^1$ is hydrogen, alkyl of 1 to 6 carbon atoms, alkoxy of 1 to 6 carbon atoms, cyano, halo, nitro, amino, or mono- or dialkylamino in which the alkyl groups have 1 to 6 carbon atoms;
$R^2$ is hydrogen, alkyl of 1 to 6 carbon atoms, phenyl, benzyl, 2-thienyl, 3-thienyl, or 2-, 3- or 4-pyridinyl;
$R^3$ is hydrogen, alkyl of 1 to 6 carbon atoms or phenyl;
$R^4$ is N-methyl-pyrrol-2-yl, 2-,3- or 4-pyridinyl, 3-quinuclidinyl or

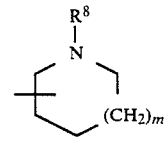

wherein
n is 1 to 5;
m is 0 to 3; and
$R^8$ is hydrogen or alkyl of 1 to 6 carbon atoms; or
$R^4$ is

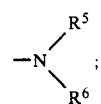

wherein
(a) n is 2, $R^5$ taken with $R^3$ is ethylene and $R^6$ is —CHO, alkyl of 1 to 6 carbon atoms, unsubstituted or substituted phenyl, pyrimidinyl, pyridinyl, or pyrazinyl where the substituents are alkyl of 1 to 6 carbon atoms, alkoxy of 1 to 6 carbon atoms, halo, cyano, nitro or trifluoromethyl;
(b) n is 1 to 5, and $R^5$ and $R^6$ taken together are polymethylene of 4 to 6 carbon atoms which may be alkyl substituted with a group having from 1 to 6 carbon atoms or $R^5$ and $R^6$ taken with the nitrogen atom to which they are attached are morpholino, 3-azabicyclo[3.2.2]nonan-3-yl, pyrrol-1-yl, pyrrolidin-2-on-1-yl, pyrrolidin-2-thion-1-yl, imidazol-1-yl, alkyl-piperidin-1-yl in which the alkyl group contains 1 to 6 carbon atoms, or a piperazin-1-yl moiety in the 4-position of which is hydrogen, —CHO, alkyl of 1 to 6 carbon atoms or unsubstituted or substituted phenyl, pyrimidinyl, pyridinyl, or pyrazinyl where the substituents are alkyl of 1 to 6 carbon atoms, alkoxy of 1 to 6 carbon atoms, halo, cyano, nitro or trifluoromethyl; or
(c) n is 1 to 5, and $R^5$ and $R^6$ are, independently, hydrogen, alkyl of 1 to 6 carbon atoms, phenyl, 3-quinuclidinyl, 2-adamantyl, bicyclo[3.2.1]octan-2-yl, bicyclo[3.3.1]nonan-9-yl or 2-, 3- or 4-pyridinyl;

or a pharmaceutically acceptable salt thereof.

Of these compounds, from the standpoint of availability of starting compounds and production economics, the preferred compounds are those of the formula:

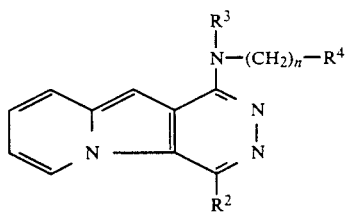

in which
$R^2$ is alkyl of 1 to 3 carbon atoms;
$R^3$ is hydrogen or alkyl of 1 to 3 carbon atoms;
$R^4$ is

wherein
$R^5$ and $R^6$ are, independently, hydrogen, alkyl of 1 to 3 carbon atoms or 3-quinuclidinyl or $R^5$ and $R^6$, taken with the nitrogen atom to which they are attached are morpholino or a piperazin-1-yl moiety in which the 4-position is substituted with an alkyl group of 1 to 3 carbon atoms or a 2-pyrimidinyl group; and
n is one of the integers 2, 3, 4 or 5;
or a pharmaceutically acceptable salt thereof.

From an activity profile, the most preferred compound is that of Example 1, infra.

The pharmaceutically acceptable salts are those conventionally produced with organic or inorganic acids such as hydrochloric, hydrobromic, sulfuric, phosphoric, nitric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like. The term halo employed on the foregoing description of the invention is intended to embrace chlorine, bromine, iodine and fluorine, the chloro or bromo groups being preferred.

The compounds of this invention may be readily prepared by displacing the halogen from the 1-position of an appropriately substituted 1-halo-pyridazino[4,5-b]indolizine with the desired amine, thusly

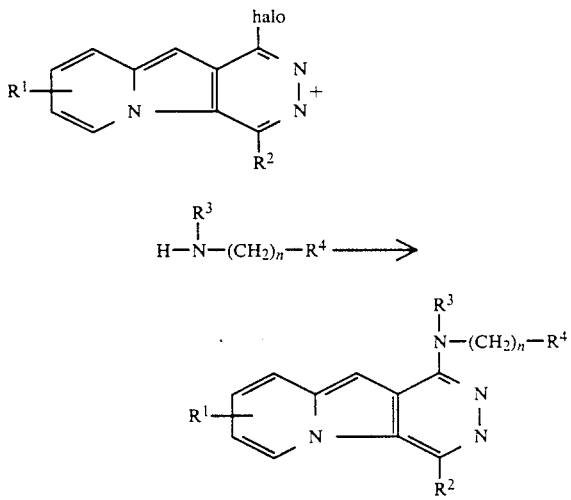

The amino reactants are commerically available or prepared by methods well known in the art. The 1-halo-pyridazino[4,5-b]indolizine reactants may be prepared by various methods known to the medicinal chemist. For example, 2-indolizinecarboxylic acid which may be variously substituted as desired [Bragg et al., J. Chem. Soc. 3277 (1963)] is converted to an ester (methanol treated with an acid such as HCl) and the product is acylated with either an acid anhydride or an acid halide [$R^4$COCl or ($R^4$CO)$_2$O] in the presence of an acid acceptor (triethylamine, etc.) or by means of the Vilsmeir-Haak reaction when $R^2$ is hydrogen, to obtain the corresponding 3-acyl-2-indolizine carboxylic acid ester. This product is treated with hydrazine hydrate to afford the corresponding substituted 2H-pyridazino[4,5-b]indolizin-1-one.

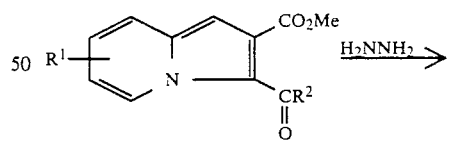

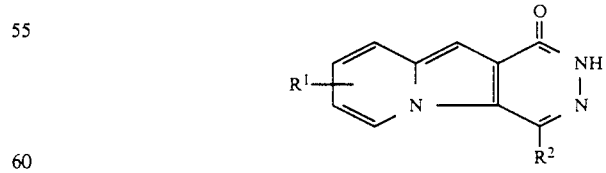

Halogenation with POCl$_3$, SOCl$_2$ and the like affords the corresponding 1-halo-pyridazino[4,5-b]indolizine reactant.

The reaction of the 1-halo-pyridazino[4,5-b]indolizine derivatives with the desired amine is performed with an excess (10-30 equivalents) of the amine at reflux temperature if the boiling point of the amine is below about 150° C., or up to about 160° C. in the melting range of the amine in an inert atmosphere. The reaction is readily followed by thin layer chromatography on silica gel (1:1 MeOH:EtOAc, 100% MeOH or MeOH containing 1-5% triethylamine or ammonium hydroxide). The reaction takes from several hours to several days to go to completion. After the reaction is complete, the excess amine is removed by vacuum distillation or extraction ($CH_2Cl_2$ with water wash) as appropriate. The organic phase is dried ($Na_2SO_4$) and evaporated in vacuo to obtain the crude product which is chromatographically purified (silica gel; acetonitrile, methanol or 1:1 MeOH:EtOAc containing an $NH_4OH$ gradient 0-7%). The product is then converted to the desired salt conventionally.

The following examples of the preparation of several compound species are presented as illustrative rather than limitative elements of the invention.

EXAMPLE 1

1-[(3'-Diethylaminopropyl)amino]-4-methyl-pyridazino[4,5-b]indolizine

A stirred solution of 2-indolizinecarboxylic acid, methyl ester (91.42 g, 0.522 mole) and anhydrous sodium acetate (42.53 g, 0.52 mole) in acetic anhydride (1.1 L) was refluxed, under anhydrous conditions, for 48 hours. After cooling most of the acetic anhydride was evaporated in vacuo. The resulting residue (150 ml) was cooled in an ice water bath and methanol (140 ml) was added to destroy the remaining acetic anhydride. The resulting mixture was poured into water (1.1 L) and the product was extracted with diethyl ether, three times. The ethereal layer was washed with saturated sodium bicarbonate solution, three times, with water, two times, and was dried over magnesium sulfate. Evaporation of solvent yielded 112 g of crude 3-acetyl-2-indolizinecarboxylic acid, methyl ester which was chromatographed on silica gel (3 kg) using 10% acetone in benzene as eluant, to afford the pure compound (85.5 g). For analysis, the product was recrystallized from a mixture of diethyl ether and petroleum ether.

Elemental analysis for $C_{12}H_{11}O_3N$ Calc'd: C, 66.35; H, 5.11; N, 6.45. Found: C, 66.21; H, 5.02; N, 6.42.

A solution of the keto ester prepared in the preceding paragraph (25.97 g, 0.119 mole) and 99% hydrazine hydrate (46 ml) in ethanol (250 ml) was refluxed for 18 hours. The resulting suspension was cooled, filtered and dried to yield (19.48 g). Evaporation of the filtrate and trituration of the resulting residue with ethanol afforded 1.07 g of additional product (total 20.55 g). For analyst, the product was recrystallized from N,N-dimethylformamide.

Elemental analysis for $C_{11}H_9ON_3$ Calc'd: C, 66.32; H, 4.55; N, 21.09. Found: C, 66.17; H, 4.55; N, 21.42.

The stirred suspension of the 4-methyl-2H-pyridazino[4,5-b]indolizine-1-one (10.0 g, 0.050 mole) in phosphoryl chloride (75 ml) was refluxed under nitrogen for 3 hours. After cooling, the reaction mixture was poured into ice-water (1 L) with vigorous stirring. Then, the solution was made alkaline (pH 8-9) by addition of a 50% W/W sodium hydroxide solution (cooling). The suspension was filtered and the solid was washed with water and dried to yield 1-chloro-4-methylpyridazino[4,5-b]indolizine (10.33 g). For analysis, a sample was recrystallized from dichloromethane and ether.

Elemental analysis for $C_{11}H_8N_3Cl$ Calc'd: C, 60.70; H, 3.70; N, 19.31. Found: C, 60.47; H, 3.68; N, 18.98.

A mixture of the chloropyridazino indolizine (500 mg, 2.3 mmoles) and 3-diethylaminopropylamine (10 ml) was refluxed for 4 hours. After cooling the excess of 3-diethylaminopropylamine was removed by distillation under high vacuum. The resulting residue (1.5 g) was dissolved in a small amount of chloroform (10 ml). Diethyl ether was added and upon scratching the free base of the title compound crystallized slowly (370 mg). This was dissolved in a small amount of methanol and a little excess of ethereal hydrogen chloride was added. Diethyl ether was added to precipitate the title product as the dihydrochloride which crystallized on scratching (457 mg), m.p. 293°-295° C. (dec), 52% yield. For analysis, the product was recryatllized from methanol and diethyl ether.

Elemental analysis for $C_{18}H_{25}N_5 \cdot 2HCl \cdot \frac{1}{4}H_2O$ Calc'd: C, 55.59; H, 7.13; N, 18.01. Found: C, 55.57; H, 7.14; N, 17.86.

EXAMPLE 2

N,N-Dimethyl-N'-(4-methylpyridazino[4,5-b]indolizin-1-yl-1,2-ethane diamine

1-Chloro-4-methylpyridazino[4,5-b]indolizine (10 g, 4.6 mmol) and N,N-dimethylethylenediamine (10.94 g, 124 mmol) were heated in a nitrogen atmosphere under reflux overnight. Excess amine was removed on a rotary evaporator at <1 mm of Hg and the solid residue was dissolved in methanol and filtered through a short pad of silica gel. The pad was washed with methanol (3×100 mL) and the product was removed by elution with 20% triethylamine in methanol. Rotary evaporation of methanol and triethylamine under aspirator vacuum gave 1.23 g (99%) of the free base as a yellow solid. The free base was dissolved in a minimum amount of methanol, treated with ethereal HCl and diluted with diethyl ether to precipitate the title compound as a dihydrochloride salt 1.28 g (91%) as a yellow solid, mp. 250°-254° C., 240° C. darken.

Elemental analysis for $C_{15}H_{19}N_5 \cdot 2HCl$ Calc'd: C, 52.64; H, 6.18; N, 20.46. Found: C, 53.27; H, 6.72; N, 20.36.

Following the procedure of the preceding paragraph with the exception that N-(2-pyridinyl)ethanediamine is employed rather than N,N-dimethylethylenediamine, affords N-(2-pyridinyl)-N'-(4-methylpyridazino[4,5-b]indolizin-1-yl-1,2-ethanediamine.

EXAMPLE 3

N,N-Dimethyl-N'-(4-methylpyridazino[4,5-b]indolizin-1-yl)-1,3-propanediamine

1-Chloro-4-methylpyridazino[4,5-b]indolizine (1.0 g, 4.6 mmol) and 3-dimethylaminopropylamine (4.7 g, 46 mmol) were combined and heated under reflux in a nitrogen atmosphere overnight. After stirring at room temperature for 2 days the excess amine was distilled off at <1 mm of Hg using a rotary evaporator. The residue was dissolved in methanol and filtered through a pad of silica gel. The pad was rinsed with methanol (3×100 mL) and then with 1:1 methanol:triethylamine (4×100 mL). The eight fractions were analyzed by thin layer chromatography on silica gel eluting with methanol/triethylamine. Fractions 4 and 5 were combined and evaporated in vacuo to give the free base as a bright yellow oil. The free base was dissolved in a minimum amount of methanol, treated with ethereal HCl and diluted with diethyl ether to give 728 mg (46%) of the title compound as a dihydrochloride salt. To obtain an analytical sample, the salt was purified by HPLC (silica, methanol containing 0–3% ammonium hydroxide) and reconverted to the dihydrochloride salt. The yield was 315 mg (20%) as yellow crystals, mp 260° C.

Elemental analysis for $C_{16}H_{21}N_5.2HCl.H_2O$ Calc'd: C, 51.34; H, 6.73; N, 18.71. Found: C, 51.01; H, 6.33; N, 18.37.

Following the procedure of the preceding paragraph with the exception that 4-dimethylaminobutylamine is employed rather than 3-dimethylaminopropylamine affords N,N-dimethyl-N'-(4-methylpyridazino[4,5-b]indolizin-1-yl)-1,4-butanediamine or a pharmaceutically acceptable salt thereof.

EXAMPLE 4

N-[2-(4-Morpholinyl)ethyl]-4-methylpyridazino[4,5-b]indolizin-1-amine

Following the procedure of Example 1, reaction of one equivalent of 1-chloro-4-methylpyridazino[4,5-b]indolizine and 27 equivalents of 4-(2-aminoethyl)morpholine gave the title compound as the free base which was converted to the dihydrochloride salt (MeOH/ethereal HCl/diethyl ether), mp 310° C. (dec.).

Elemental analysis for $C_{17}H_{21}N_5O.2HCL.H_2O$ Calc'd: C, 50.75; H, 6.26; N, 17.41. Found: C, 50.78; H, 5.89; N, 17.51.

EXAMPLE 5

N-[3-(4-Morpholinyl)propyl]-4-methylpyridazino[4,5-b]indolizin-1-amine

Following the procedure of Example 1, reaction of one equivalent of 1-chloro-4-methylpyridazino[4,5-b]indolizine and 10 equivalents of 4-(3-aminopropyl)morpholine gave the title compound as the free base which was converted to the dihydrochloride salt, mp. 295°–296° C. (after recrystallization from ethanol).

Elemental analysis for $C_{18}H_{23}N_5O.2HCl$ Calc'd: C, 54.27; H, 6.33; N, 17.58. Found: C, 53.90; H, 6.26; N, 17.41.

EXAMPLE 6

N-[(1-Ethyl-2-pyrrolidinyl)methyl]-4-methyl-pyridazino[4,5-b]-indolizin-1-amine

Following the procedure of Example 1, reaction of one equivalent of 1-chloro-4-methylpyridazino[4,5-b]indolizine and 27 equivalents of 2-(aminomethyl)-1-ethylpyrrolidine gave the title compound as the free base which was converted to the dihydrochloride salt, mp. 128° C. (dec.).

Elemental analysis for $C_{18}H_{23}N_5.2HCl.1.75H_2O$ Calc'd: C, 52.24; H, 6.94; N, 16.92. Found: C, 52.30; H, 6.39; N, 16.55.

EXAMPLE 7

4-Methyl-1-(4'-methylpiperazinyl)pyridazino[4,5-b]indolizine

Following the procedure of Example 1, reaction of one equivalent of 1-chloro-4-methylpyridazino[4,5-b]indolizine and 10 equivalents of 1-methylpiperazine gave the title compound as the free base as a yellow solid, mp. 110° C. in 61% yield after flash chromatography (silica gel, 0–1.2% NH4OH in acetonitrile). The free base was converted to the dihydrochloride salt (MeOH/ethereal HCl/diethyl ether), mp. 343°–344° C.

Elemental analysis for $C_{16}H_{19}N_5.2HCl$ Calc'd: C, 52.24; H, 6.26; N, 19.77. Found: C, 53.92; H, 6.01; N, 19.41.

EXAMPLE 8

4-Methyl-N-[3-(1-piperidinyl)propyl]pyridazino[4,5-b]indolizin-1-amine

Following the procedure of Example 1, reaction of one equivalent of 1-chloro-4-methylpyridazino[4,5-b]indolizine and 10 equivalents of 1-(3-aminopropyl)piperidine at 130° C. gave the title compound as the free base (oil, 83%) after HPLC purification. Trituration with hexane gave a yellow solid (50%), mp 130°–134° C. The free base was then converted to the dihydrochloride salt (MeOH/ethereal HCl/diethyl ether), mp. 302°–303° C.

Elemental analysis for $C_{19}H_{25}N_5.2HCl.0.5H_2O$ Calc'd: C, 56.30; H, 6.96; N, 17.28. Found: C, 55.97; H, 6.85; N, 16.94.

Following the procedure of Example 8 with the exception that instead of 1-(3-aminopropyl)piperidine, 1-(3-aminopropyl)-2-methyl-piperidine, 1-(3-aminopropyl)pyrrolidine or 1-(4-aminobutyl)pyrrolidine are employed as the reactant to obtain 4-methyl-N-[3-(2-methylpiperidin-1-yl)propyl]pyridazino[4,5-b]-indolizin-1-amine, or a pharmaceutically acceptable salt thereof; 4-methyl-N-[3-(1-pyrrolidinyl)propyl]-pyridazino[4,5-b]-indolizin-1-amine, or a pharmaceutically acceptable salt thereof; or 4-methyl-N-[4-(1-pyrrolidinyl)butyl]pyridazino[4,5-b]-indolizin-1-amine, or a pharmaceutically acceptable salt thereof.

EXAMPLE 9

4-Methyl-N-[4'-methyl(1-piperazinyl)propyl]-pyridazino[4,5-b]indolizin-1-amine

Following the procedure of Example 1, reaction of one equivalent of 1-chloro-4-methylpyridazino[4,5-b]indolizine and 10 equivalents of 4-methyl-1-(3-aminopropyl)piperazine at 150° C. gave the title compound as the free base (yellow solid, 16% of theory) after purification by HPLC and trituration with i-propylether, mp 60° C. (foams). The free base was converted to the trihydrochloride salt mp. 280° C., 275° C. shrink (hydroscopic).

Elemental analysis for $C_{19}H_{26}N_6.3HCl.2.5H_2O$ Calc'd: C, 46.30; H, 6.95; N, 17.05. Found: C, 46.48; H, 7.20; N, 17.09.

EXAMPLE 10

4-Methyl-N-[4'-methyl(1-piperazinyl)butyl]-pyridazino[4,5-b]indolizin-1-amine

Reaction of 1-chloro-4-methylpyridazino[4,5-b]indolizine (1.5 g, 6.89 mmol) and 4-methyl-1-(4-aminobutyl)piperazine (11.80 g, 68.9 mmol) gave 0.810 g (34%) of the title compound as the free base (yellow solid, mp 110°–111° C.) after HPLC trihydrochloride salt (MeOH/ethereal HCl/diethyl ether), mp 282°–283° C., 280° C. shrinks.

Elemental analysis for $C_{20}H_{28}N_6.3HCl.1.5H_2O$ Calc'd: C, 49.13; H, 7.01; N, 17.19. Found: C, 49.09; H, 6.82; N, 17.17.

EXAMPLE 11

4-(4-Methylpyridazino[4,5-b]indolizin-1-yl)-piperazinecarboxaldehyde

Following the procedure of Example 1, reaction of one equivalent of 1-chloro-4-methylpyridazino[4,5-b]indolizine and 10 equivalents of piperazinecarboxaldehyde at 150° C. gave the title compound as the free base, which was purified by flash chromatography (silica gel, 1 to 20% methanol:ethyl acetate) and converted to the dihydrochloride salt (MeOH/etheral HCl/diethyl ether), mp 325° C.

Elemental analysis for $C_{16}H_{17}N_5O.2HCl.H_2O$ Calc'd: C, 49.75; H, 5.48; N, 18.13. Found: C, 49.51; H, 4.93; N, 17.85.

EXAMPLE 12

N-(1-Azabicyclo[2.2.2]oct-3-yl)-N'-(4-methylpyridazino[4,5-b]indolizin-1-yl)-1,2-ethanediamine To a solution of 3-quinuclidinone hydrochloride (600 mg, 3.7 mmol) in methanol (15 mL) was added a solution of N-(4-methylpyridazino[4,5-b]indolizin-1-yl)-1,2-ethanediamine (900 mg, 3.7 mmol) in methanol (11 mL) over a one minute period at room temperature. After stirring for 5 to 10 minutes, a solution of zinc modified cyanoborohydride (8.7 mL of 0.50M cyanoborohydride in methanol, 4.4 mmol) was added [Kim, et al., J. Org. Chem. 50, 1927 (1985)]. A yellow precipitate formed. After stirring for 4 days at room temperature, 50% sodium hydroxide (1 mL) was added and the solvent was evaporated. The residue was mixed with 4:1 chloroform:methanol (at 20 mL) and filtered through a plug of basic alumina. The filtrate was evaporated and the residue was purified by flash chromatography (alumina, 4:1 chloroform:methanol to 100% methanol) to give the title compound as the free base which was converted to the fumaric acid salt (fumaric acid/ethanol), mp 205°–208° C.

Elemental analysis for $C_{20}H_{26}N_6.2C_4H_4O_4.1\frac{1}{2}H_2O$ Calc'd: C, 55.16; H, 6.11; N, 13.78. Found: C, 55.50; H, 5.82; N, 13.85.

Employing N-(4-methylpyridazino[4,5-b]indolizin-1-yl)-1,2-propanediamine gives N-(1-azabicyclo[2.2.2]oct-3-yl)-N'-(4-methylpyridazino[4,5-b]indolizin-1-yl)-1,2-propanediamine, as the free base.

EXAMPLE 13

N-(1-Methylpyridazino[4,5-b]indolizin-4-yl)-N'-(tricyclodec-1-yl)-1,2-ethanediamine Following the procedure of Example 12, adamantanone (570 mg, 3.8 mmol) in methanol (11 mL) was added to a solution of N-(4-methylpyridazino[4,5-b]indolizin-1-yl)-1,2-ethanediamine in methanol (10 mL) to give after 24 hours at room temperature the title compound as the free base. After purification by chromatography (neutral alumina, 99:1 chloroform:methanol) it was converted to the fumarate salt (fumaric acid/ethanol), mp >250° C.

Elemental analysis for $C_{23}H_{29}N_5.C_4H_4O_4.1\frac{1}{2}H_2O$ Calc'd: C, 62.53; H, 7.00; N, 13.51. Found: C, 62.28; H, 6.81; N, 13.54.

Following the procedure of the preceding paragraph with the exception that bicyclo(3.3.1)non-9-one is employed rather than adamantanone affords N-(bicyclo(3.3.1)non-9-yl)-N'-(4-methylpyridazino[4,5-b]indolizin-1-yl)-1,2-ethanediamine as the free base. It is converted to the dihydrochloride 1.25 hydrate by conventional means.

EXAMPLE 14

4-Methyl-N-[2-[4-(2-pyrimidinyl)-1-piperazinyl]ethyl]-pyridazino[4,5-b]indolizin-1-amine 1-Chloro-4-methylpyridazine (2 g, 9 mmol) and 1-(2-pyrimidyl)-4-(2'-aminoethyl)piperazine (3.8 g, 18 mmol) in N-methylpyrrolidinone (1 mL) was heated at 150° C. for 1.5 days. After removal of the solvent under vacuum, the residue was partitioned between methylene chloride and water. The organic phase was washed with saturated sodium bicarbonate solution, dried, and evaporated to give the title compound as the free base. After purification by HPLC (silica, 0.2% methanol:ethyl acetate) the compound was converted to the trihydrochloride salt (methanol/etheral HCl/diethyl ether) and recrystallized from methanol/isopropyl ether, mp 280°–283° C.

Elemental analysis for $C_{21}H_{24}N_8.3HCl.3H_2O$ Calc'd: C, 45.70; H, 6.06; N, 20.30. Found: C, 45.65; H, 5.28; N, 20.16.

EXAMPLE 15

N-[3-(3-Azabicyclo[3.2.2]non-3-yl)propyl]-4-methyl-pyridazino[4,5-b]indolizin-1-amine Following the procedure of Example 1, reaction of one equivalent of 1-chloro-4-methylpyridazino[4,5-b]indolizine and 3 equivalents of 3-(3-azabicyclo[3.2.2]non-3-yl)propylamine at 150° C. overnight gave the title compound as the free base which was purified by chromatography (silica gel, 1:4 methanol:methylene chloride containing ammonium hydroxide) and converted to the dihydrochloride salt (ethanol/etheral HCl), mp 343° C. dec.

Elemental analysis for $C_{22}H_{29}N_5.2HCl.H_2O$ Calc'd: C, 58.14; H, 7.32; N, 15.41. Found: C, 58.18; H, 7.25; N, 15.59.

EXAMPLE 16

N-(Bicyclo[3.2.1]oct-2-yl)-N'-(4-methylpyridazino[4,5-b]indolizin-1-yl) 1,2-ethanediamine Following the procedure of Example 12, bicyclo[3.2.1]octan-2-one in methanol (3 to 4 mL) was added to a solution of N-(4-methylpyridazino[4,5-b]indolizin-1-yl)-1,2-ethanediamine hydrochloride in methanol/DMSO (90 mL:30 mL) which had been heated to boiling and then allowed to cool. After stirring at room temperature overnight, the title compound was obtained as the free base after column chromatography (silica gel, 4:1 methylene chloride:methanol to 100% methanol containing ammonium hydroxide) and recrystallized from isopropyl ether. The compound was converted to the dihydrochloride salt by ethanolic HCl, mp 339°–344° C.

Elemental analysis for $C_{21}H_{27}N_5.2HCl.2H_2O$ Calc'd: C, 59.21; H, 6.96; N, 16.44. Found: C, 59.22; H, 6.82; N, 16.52.

EXAMPLE 17

1-[3-[(1-Methylpyridazino[4,5-b]indolizin-4-yl)amino]-propyl-2-pyrrolidinone

Following the procedure of Example 1, reaction of one equivalent of 1-chloro-4-methylpyridazino[4,5-b]indolizine, five equivalents of 1-(3-aminopropyl)pyrrolidinone, and one quivalent of ammonium chloride at reflux under nitrogen for 3 hours gave the title compound as the free base after flash column chromatography (silica gel, methanol:ethyl acetate). This was converted to the hydrochloride salt, mp 257°–258° C.

Elemental analysis for $C_{18}H_{20}N_5O\cdot HCl\cdot 5/4H_2O$ Calc'd: C, 56.59; H, 5.95; N, 18.05. Found: C, 56.69; H, 6.21; N, 18.37.

Following the same procedure of the preceding paragraph, employing 1-(3-aminopropyl)-2-pyrrolidinethione, 1-[3-[(1-methylpyridazino[4,5-b]indolizin-4-yl)amino]-propyl-2-pyrrolidinethione is obtained.

Similarly, employing 1-pyrrolylpropylamine affords 1-[3-[(1-methylpyridazino[4,5-b]indolizin-4-yl)amino]-propyl pyrrole, or a pharmaceutically acceptable salt thereof;

EXAMPLE 18

N-[4-(3-Azabicyclo[3.2.2]non-3-yl)butyl]-4-methylpyridazino[4,5-b]indolizin-1-amine Following the procedure of Example 1, reaction of one equivalent of 1-chloro-4-methylpyridazino[4,5-b]indolizine, three equivalents of 4-(3-azabicyclo[3.2.2]non-3-yl)butylamine and one equivalent of ammonium chloride at 145° C. under nitrogen overnight gave the title compound as the free base after flash column chromatography (silica gel, 4:1 methylene chloride:methanol to 100% methanol containing ammonium hydroxide). This was converted to the dihydrochloride salt and recrystallized from ethanol, mp 257°–258° C.

Elemental analysis for $C_{23}H_{31}N_5\cdot 2HCl\cdot 2.3H_2O$ Calc'd: C, 56.11; H, 7.71; N, 14.23. Found: C, 56.12; H, 7.75; N, 14.09.

EXAMPLE 19

4-Methyl-N-[2-(1-methyl-2-pyrrolidinyl)ethyl]-pyridazino[4,5-b]indolizin-1-amine Following the procedure of Example 1, reaction of one equivalent of 1-chloro-4-methylpyridazino[4,5-b]indolizine, ten equivalents of 2-(1-methyl-2-pyrrolidinyl)ethylamine and one equivalent of ammonium chloride under reflux in a nitrogen atmosphere for 3 to 4 hours gave the title compound as the free base after removal of excess amine in vacuo and treatment of the residue with boiling ethyl acetate. The solid collected upon filtration was converted to the hydrochloride salt (methanol/ethereal HCl/ether), mp 169° C.

Elemental analysis for $C_{18}C_{19}N_5\cdot HCl\cdot \frac{1}{2}H_2O$ Calc'd: C, 61.62; H, 6.03; N, 19.53. Found: C, 61.70; H, 5.92; N, 19.64.

Following the procedure of the preceding paragraph, with the exception that, instead of 2-(1-methyl-2-pyrrolidinyl)ethylamine, 2-(1-methyl-2-pyrrolyl)ethylamine is employed yields 4-methyl-N-[2-(1-methyl-2-pyrrolyl)ethyl]pyridazino[4,5-b]indolizin-1-amine as the free base. The hydrochloride salt is obtained by conventional means.

Similarly, substitution of 2-pyridinylethylamine for 2-(1-methyl-2-pyrrolidinyl)ethylamine affords 4-methyl-N-[2-(2-pyridinyl)ethyl]pyridazino[4,5-b]indolizin-1-amine.

EXAMPLE 20

4-Methyl-N-[3-(1H-imidazol-1-yl)propyl]-pyridazino[4,5-b]indolizine

Following the procedure of Example 1, reaction of one equivalent of 1-chloro-4-methylpyridazino[4,5-b]indolizine, eight equivalents of 3-(1H-imidazol-1-yl)propylamine and one equivalent of ammonium chloride under reflux in a nitrogen atmosphere for 1 hour and at room temperature for 48 hours gave the title compound as the free base after removal of excess amine in vacuo and purification by flash chromatography (silica gel, 10 to 40% methanol in ethyl acetate). The free base was converted to the dihydrochloride salt (methanol/ethereal HCl/diethyl ether), mp 162°–163° C.

Elemental analysis for $C_{17}H_{18}N_6\cdot 2HCl\cdot \frac{3}{4}H_2O$ Calc'd: C, 51.98; H, 5.52; N, 21.40. Found: C, 51.82; H, 5.30; N, 21.23.

EXAMPLE 21

N-(4-Morpholino)butyl-4-methylpyridazino[4,5-b]indolizin-1-amine

Following the procedure of Example 1, reaction of one equivalent of 1-chloro-4-methylpyridazinyl[4,5-b]indolizine and a large excess of 4-(4-aminobutyl)morpholine gives the title compound as the free base which may be converted to the dihydrochloride salt by conventional means.

EXAMPLE 22

4-Methyl-N-[2-[4-(2-pyrimidinyl)-1-piperazinyl]-propyl]pyridazino[4,5-b]indolizin-1-amine Following the procedure of Example 14, 1-chloro-4-methylpyridazinyl[4,5-b]indolizine is reacted with 1-(2-pyrimidyl)-4-(2'-aminopropyl)piperazine in N-methylpyrrolidione to obtain the title compound as the free base. Conversion to the hydrochloride is accomplished conventionally.

EXAMPLE 23

(a)

N-[(1-Azabicyclo[2.2.2]oct-3-yl-methyl]-4-methylpyridazino[4,5-b]indolizin-1-amine (b)

N-[(1-Azabicyclo[2.2.2]oct-3-yl-ethyl]-4-methylpyridazino[4,5-b]indolizin-1-amine The title compounds are prepared following the procedure of Example 1, by reaction of one equivalent of 1-chloro-4-methylpyridazinyl[4,5-b]indolizine with a large excess of quinuclidin-3-ylmethylamine or quinuclidin-3-ylethylamine, respectively to yield the free bases which are readily converted to the hydrochloride salts by conventional means.

The selective $M_1$ muscarinic binding by the compounds of this invention was established by determining the $IC_{50}$ concentration of the test compound that will cause a fifty percent inhibition of specific [$^3$H]pirenzepine binding to rat brain tissue ($IC_{50}$). Similarly, the $IC_{50}$ value was determined for $M_2$ receptor binding at cerebellum tissue which contains a high portion of $M_2$ receptors, relative to [$^3$H]quinuclidinyl benzilate (QNB). Comparison of the results obtained in these in vitro studies indicates the relative selectivity of the test compound for binding at the post-synaptic cholinergic $M_1$ receptors which are mainly found in the central nervous system. The results of these studies were as follows:

TABLE 1

| Compound | [$^3$H]-Pirenzepine $M_1$ $IC_{50}$ μM | [$^3$H]QNB $M_2$ $IC_{50}$ μM | M2/M1 |
|---|---|---|---|
| Example 1 | 0.098 | 4.1 | 42 |
| Example 2 | 0.66 | 12 | 18 |

TABLE 1-continued

| Compound | [³H]-Pirenzepine M₁ IC₅₀ μM | [³H]QNB M₂ IC₅₀ μM | M2/M1 |
|---|---|---|---|
| Example 3 | 0.6 | 9.5 | 24 |
| Example 4 | 2.45 | 19 | 8 |
| Example 5 | 0.27 | 12 | 44 |
| Example 6 | 0.26 | 6.2 | 24 |
| Example 7 | 1.0 | 29 | 29 |
| Example 8 | 0.11 | 1.4 | 13 |
| Example 9 | 0.15 | 2.8 | 19 |
| Example 10 | 0.14 | 3.5 | 25 |

In addition, the compound of Example 1 was tested, as representative of the other compounds of the invention, to establish its ability to reduce scopolamine-induced hyperactivity which is currently considered a muscarinic M¹-mediated effect. Thus, after thirty minutes of habituation to locomotor activity chambers (Digiscan, Omnitech; Columbus, Ohio), rats, employed as standard test animals, were given either vehicle alone, scopolamine alone (1.7 mg/kg, s.c.), or both scopolamine and one dose of the compound being tested and the animals were returned to the chambers for an additional hour.

The motor activity chambers utilize infrared detectors to assess movement in 3 axes. Total activity measures (vertical+horizontal activity) were collected in 15 minute intervals for 1 hour post-injection. Total activity measures were cumulated across all time intervals for statistical analysis.

Scopolamine at the dose used produced a significant increase in the total activity measure. A test compound is considered active as an M₁ agonist if it produces an attenuation of scopolamine-induced hyperactivity, i.e., if total activity is statistically lower than scopolamine-only controls or does not differ from vehicle-only controls.

The compound of Example 1 was thereby established to be active at 30 and 54 mg/kg doses i.p. to produce sufficient reduction in hyperactivity. That total activity did not differ from vehicle-only controls. Arecoline is active in this test procedure at about 5.4 mg/kg.

The compound of Example 1 was also studied in the radial arm maze test where male Sprague-Dawley (Charles River) rats on a 23-hour food deprivation schedule were trained in an eight arm radial maze with all arms baited. Each session consisted of two maze exposures, with a time limit of 500 seconds for each exposure. After four correct choices (first exposure), each animal was removed from the maze for one hour then returned with only the remaining four arms baited (second exposure). Choice errors, consisting of delay errors (re-entry into any of the four arms chosen during the first exposure) and current errors (re-entry into any of the four arms chosen during the second exposure), as well as total errors were recorded. Durations for each exposure were also recorded. Statistical analysis were preformed using a One-Way Anova with Dunnetts T-Test comparisons.

In experiments to assess standards, scopolamine HBr (0.3 mg/kg) was administered subcutaneously 30 minutes prior to the test, while arecoline (10 mg/kg) and physostigmine (0.01 mg/kg) were administered intraperitoneally 15 mintues prior to the test. In a subsequent experiment, scopolamine HBr (0.3 mg/kg, s.c.) and the compound of Example 1 (1, 3, 10 mg/kg, i.p.) were administered simultaneously 30 minutes prior to the test. All compounds were solubilized in distilled water.

In the first experiment, the scopolamine only group produced a significant increase in delay, current and total errors versus vehicle, while the arecoline and physostigmine groups did not (Table 2). In fact, arecoline and physostigmine produced a significant reduction in scopolamine impairment in delay, current and total errors. Scopolamine treatment also increased all time measures compared to vehicle. Physostigmine produced a significant time reduction compared to scopolamine in both delay time (first exposure) and total time. The arecoline group showed a significant time increase versus vehicle with no significant time reduction versus scopolamine.

In the experiment with the compound in Example 1 (Table 3), scopolamine significantly increased total errors compared to vehicle. The Example 1 compound reduced the impairment caused by scopolamine (i.e., scopolamine plus drug not different than vehicle), at all doses tested, but not so much that the drug groups were significantly different than the scopolamine only group. Delay errors showed no dose-related trend, however, current and total errors demonstrated a definite dose-related decrease in scopolamine impairment with the 10 mg/kg dose being the most potent. Scopolamine also increased all time measures compared to vehicle. Delay time (first exposure) scores were also significantly increased in the Example 1 3.0 mg/kg dose group. Current time (second exposure) was significantly increased in all groups. The total time was significantly increased in the 3.0 and 10 mg/kg dose groups but the 1.0 mg/kg dose produced a reduction in time impairment compared to scopolamine.

These data demonstrate that the compound of Example 1 can reduce cognitive impairment due to cholinergic hypofunction.

TABLE 2

Mean Values for Arecoline and Physostigime in Radial Arm Maze

| Treatment | Dose (mg/kg) | Mean Errors | | | Mean Time (Min) | | |
|---|---|---|---|---|---|---|---|
| | | Delay | Current | Total | Delay | Current | Total |
| Vehicle | — | 0.70 | 0 | 0.70 | 0.74 | 0.99 | 1.96 |
| Scopolamine | 0.3 | 2.75* | 3.63* | 6.38* | 2.28* | 2.78* | 5.27* |
| Arecoline | 10.0 | 1.50+ | 0.75+ | 2.25+ | 1.50 | 2.32* | 4.06* |
| Physostigmine | 0.01 | 1.13+ | 0.88+ | 2.00+ | 1.14+ | 2.01 | 3.25+ |

TABLE 3

| Treatment | Dose (mg/kg) | Mean Values for Example 1 Compound in Radial Arm Maze | | | | | |
|---|---|---|---|---|---|---|---|
| | | Mean Errors | | | Mean Time (Min) | | |
| | | Delay | Current | Total | Delay | Current | Total |
| Vehicle | — | 0.67 | 0 | 0.67 | 0.62 | 0.58 | 1.47 |
| Scopolamine | 0.3 | 2.14 | 3.57 | 5.72* | 2.01* | 2.90* | 5.14* |
| Example 1 | 1.0 | 1.83 | 2.00 | 3.67 | 1.03 | 1.83* | 2.99+ |
| Example 1 | 3.0 | 2.38* | 1.13 | 3.50 | 1.95* | 2.92* | 4.96* |
| Example 1 | 10.0 | 2.00 | 0.75 | 2.75 | 1.63 | 3.32* | 5.15* |

*Significantly different vs. vehicle at p <.05.
+Significantly different vs. scopolamine at p <.05.

The compound of Example 1 was also shown by standard experimental procedures to inhibit blood platelet aggregation induced by collagen ($ED_{50}$ at about a 3 molar concentration). Thus, the property of this compound as an antithrombotic agent is indicated as an additional advantage for use in patients suffering from dementia where the possibility of thrombus formation is to be avoided as in cardiovascular disease states, as well as head trauma, and the like.

To determine the effective amount of compound to be administered prophylactically to arrest declining congnitive function as in Alzheimer's dementia, a subjective approach is taken by relating the drug dosage to improve memory responses or analogous desired responses which can be related to relief of undesirable symptoms. Based upon the animal data obtained to date, the initial dosing will begin at about 30 mg/kg oral with incremental increases until the desired result is achieved.

What is claimed is:

1. A compound of the formula:

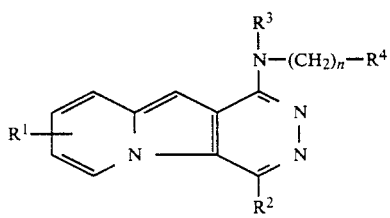

in which $R^1$ is hydrogen, alkyl of 1 to 6 carbon atoms, alkoxy of 1 to 6 carbon atoms, cyano, halo, nitro, amino, or mono- or dialkylamino in which the alkyl groups have 1 to 6 carbon atoms;

$R^2$ is hydrogen, alkyl of 1 to 6 carbon atoms, phenyl, benzyl, 2-thienyl, 3-thienyl, or 2-, 3- or 4-pyridinyl;

$R^3$ is hydrogen, alkyl of 1 to 6 carbon atoms or phenyl;

$R^4$ is N-methyl-pyrrol-2-yl, 2-, 3- or 4-pyridinyl, 3-quinuclidinyl or

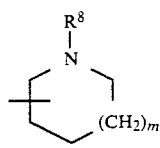

wherein
n is 1 to 5;
m is 0 to 3; and
$R^8$ is hydrogen or alkyl of 1 to 6 carbon atoms; or
$R^4$ is

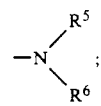

wherein
(a) n is 2, $R^5$ taken with $R^3$ is ethylene and $R^6$ is —CHO, alkyl of 1 to 6 carbon atoms, unsubstituted or substituted phenyl, pyrimidinyl, pyridinyl, or pyrazinyl where the substituents are alkyl of 1 to 6 carbon atoms, alkoxy of 1 to 6 carbon atoms, halo, cyano, nitro or trifluoromethyl;

(b) n is 1 to 5, and $R^5$ and $R^6$ taken together are polymethylene of 4 to 6 carbon atoms which may be alkyl substituted with a group having from 1 to 6 carbon atoms or $R^5$ and $R^6$ taken with the nitrogen atom to which they are attached are morpholino, 3-azabicyclo[3.2.2]nonan-3-yl, pyrrol-1-yl, pyrrolidin-2-on-1-yl, pyrrolidin-2-thion-1-yl, imidazol-1-yl, or a piperazin-1-yl moiety in the 4-position of which is hydrogen, —CHO, alkyl of 1 to 6 carbon atoms or unsubstituted or substituted phenyl, pyrimidinyl, pyridinyl, or pyrazinyl where the substituents are alkyl of 1 to 6 carbon atoms, alkoxy of 1 to 6 carbon atoms, halo, cyano, nitro or trifluoromethyl;

(c) n is 1 to 5, and $R^5$ and $R^6$ are, independently, hydrogen, alkyl of 1 to 6 carbon atoms, phenyl, 3-quinuclidinyl, 2-adamantyl, bicyclo[3.2.1]octan-2-yl, bicyclo[3.3.1]nonan-9-yl or 2-, 3- or 4-pyridinyl;

or a pharmaceutically acceptable salt thereof.

2. A compound of claim 1 of the formula:

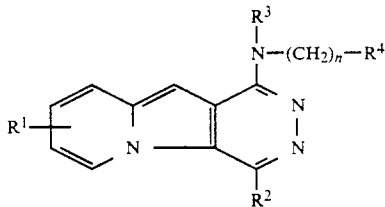

in which
$R^2$ is alkyl of 1 to 3 carbon atoms;
$R^3$ is hydrogen or alkyl of 1 to 3 carbon atoms;
$R^4$ is

wherein
R⁵ and R⁶ are, independently, hydrogen, alkyl of 1 to 3 carbon atoms or 3-quinuclidinyl or R⁵ and R⁶, taken with the nitrogen atom to which they are attached are morpholino or a piperazin-1-yl moiety in which the 4-position is substituted with an alkyl group of 1 to 3 carbon atoms, or a 2-pyrimidinyl group; and n is one of the integers 2, 3, 4 or 5;
or a pharmaceutically acceptable salt thereof.

3. A compound of claim 1 which is:
1-[(3-diethylaminopropyl)amino]-4-methylpyridazino[4,5-b]indolizine or a pharmaceutically acceptable salt thereof;
N,N-dimethyl-N'-(4-methylpyridazino[4,5-b]indolizin-1-yl-1,2-ethane diamine, or a pharmaceutically acceptable salt thereof;
N,N-dimethyl-N'-(4-methylpyridazino[4,5-b]indolizin-1-yl)-1,3-propanediamine, or a pharmaceutically acceptable salt thereof; or
N,N-dimethyl-N'-(4-methylpyridazino[4,5-b]indolizin-1-yl)-1,4-butanediamine, or a pharmaceutically acceptable salt thereof.

4. A compound of claim 1 which is:
N-[2-(4-morpholinyl)ethyl]-4-methylpyridazino[4,5-b]indolizin-1-amine, or a pharmaceutically acceptable salt thereof;
N-[3-(4-morpholinyl)propyl]-4-methylpyridazino[4,5-b]indolizin-1-amine, or a pharmaceutically acceptable salt thereof.

5. A compound of claim 1 which is N-(4-morpholino)butyl-4-methylpyridazino[4,5-b]indolizin-1-amine, or a pharmaceutically acceptable salt thereof.

6. A compound of claim 1 which is:
N-[(1-ethyl-2-pyrrolidinyl)methyl]-4-methylpyridazino[4,5-b]indolizin-1-amine, or a pharmaceutically acceptable salt thereof; or
4-methyl-N-[2-(1-methyl-2-pyrrolidinyl)ethyl]-pyridazino[4,5-b]indolizin-1-amine, or a pharmaceutically acceptable salt thereof.

7. A compound of claim 1 which is:
4-methyl-1-(4'-methylpiperazinyl)pyridazino[4,5-b]indolizine, or a pharmaceutically acceptable salt thereof; or
4-(4-methylpyridazino[4,5-b]indolizin-1-yl)-piperazinecarboxaldehyde, or a pharmaceutically acceptable salt thereof.

8. A compound of claim 1 which is:
4-methyl-N-[4'-methyl(1-piperazinyl)propyl]-pyridazino[4,5-b]-indolizin-1-amine, or a pharmaceutically acceptable salt thereof; or
4-methyl-N-[4'-methyl(1-piperazinyl)butyl]-pyridazino[4,5-b]indolizin-1-amine, or a pharmaceutically acceptable salt thereof.

9. A compound of claim 1 which is 4-methyl-N-[2-[4-(2-pyrimidinyl)-1-piperazinyl]ethyl]pyridazino[4,5-b]indolizin-1-amine, or a pharmaceutically acceptable salt thereof.

10. A compound of claim 1 which is 4-methyl-N-[2-[4-(2-pyrimidinyl)-1-piperazinyl]propyl]pyridazino[4,5-b]indolizin-1-amine, or a pharmaceutically acceptable salt thereof.

11. A compound of claim 1 which is:
4-methyl-N-[3-(1-piperidinyl)propyl]pyridazino[4,5-b]-indolizin-1-amine, or a pharmaceutically acceptable salt thereof;

N-[3-(3-azabicyclo[3.2.2]non-3-yl)propyl]-4-methylpyridazino[4,5-b]indolizin-1-amine, or a pharmaceutically acceptable salt thereof;
N-[4-(3-azabicyclo[3.2.2]non-3-yl)butyl]-4-methylpyridazino[4,5-b]indolizin-1-amine, or a pharmaceutically acceptable salt thereof;
4-methyl-N-[3-(2-methylpiperidin-1-yl)propyl]-pyridazino[4,5-b]indolizin-1-amine, or a pharmaceutically acceptable salt thereof;
4-methyl-N-[3-(1-pyrrolidinyl)propyl]pyridazino[4,5-b]-indolizin-1-amine, or a pharmaceutically acceptable salt thereof; or
4-methyl-N-[4-(1-pyrrolidinyl)butyl]pyridazino[4,5-b]-indolizin-1-amine, or a pharmaceutically acceptable salt thereof.

12. A compound of claim 1 which is N-(1-azabicyclo[2.2.2]oct-3-yl)-N'-(4-methylpyridazino[4,5-b]indolizin-1-yl)-1,2-ethanediamine, or a pharmaceutically acceptable salt thereof.

13. A compound of claim 1 which is N-(1-azabicyclo[2.2.2]oct-3-yl)-N'-(4-methylpyridazino[4,5-b]indolizin-1-yl)-1,2-propanediamine, or a pharmaceutically acceptable salt thereof.

14. A compound of claim 1 which is:
N-[(1-azabicyclo[2.2.2]oct-3-yl-methyl]-4-methylpyridazino[4,5-b]-indolizin-1-amine, or a pharmaceutically acceptable salt thereof; or
N-[(1-azabicyclo[2.2.2]oct-3-yl-ethyl]-4-methylpyridazino[4,5-b]-indolizin-1-amine, or a pharmaceutically acceptable salt thereof.

15. A compound of claim 1 which is:
N-(1-methylpyridazino[4,5-b]indolizin-4-yl)-N'-(tricyclodec-1-yl)-1,2-ethanediamine, or a pharmaceutically acceptable salt thereof;
N-(bicyclo[3.2.1]oct-2-yl)-N'-(4-methylpyridazino[4,5-b]indolizin-1-yl)-1,2-ethanediamine, or a pharmaceutically acceptable salt thereof; or
N-(bicyclo[3.3.1]non-9-yl-N'-(4-methylpyridazino[4,5-b]indolizin-1-yl-1,2-ethanediamine, or a pharmaceutically acceptable salt thereof.

16. A compound of claim 1 which is:
1-[3-[(1-methylpyridazino[4,5-b]indolizin-4-yl)amino]-propyl-2-pyrrolidinone, or a pharmaceutically acceptable salt thereof;
4-methyl-N-[3-(1H-imidazol-1-yl)propyl]-pyridazino[4,5-b]indolizine, or a pharmaceutically acceptable salt thereof;
4-methyl-N-[2-(1-methyl-2-pyrrolidinyl)ethyl]-pyridazino[4,5-b]indolizin-1-amine, or a pharmaceutically acceptable salt thereof;
1-[3-[(1-methylpyridazino[4,5-b]indolizin-4-yl)amino]-propyl-2-pyrrolidinethione, or a pharmaceutically acceptable salt thereof;
1-[3-[(1-methylpyridazino[4,5-b]indolizin-4-yl)amino]-propyl pyrrole, or a pharmaceutically acceptable salt thereof;
4-methyl-N-[2-(1-methyl-2-pyrrolyl)ethyl]-pyridazino[4,5-b]indolizin-1-amine, or a pharmaceutically acceptable salt thereof.

17. A compound of claim 1 which is:
4-methyl-N-[2-(2-pyridinyl)ethyl]pyridazino[4,5-b]indolizin-1-amine, or a pharmaceutically acceptable salt thereof; or
N-(2-pyridinyl)-N'-(4-methylpyridazino[4,5-b]indolizin-1-yl-1,2-ethanediamine, or a pharmaceutically acceptable salt thereof.

* * * * *